US010813781B2

(12) United States Patent
Pattison et al.

(10) Patent No.: US 10,813,781 B2
(45) Date of Patent: Oct. 27, 2020

(54) SLEEVE-ANCHORABLE GASTRIC BALLOON FOR WEIGHT LOSS

(71) Applicant: EZ-OFF WEIGHT LOSS, LLC, Leawood, KS (US)

(72) Inventors: Mary J. Pattison, Kansas City, MO (US); Charles Phillip Pattison, Kansas City, MO (US); Mark Molos, Kansas City, MO (US)

(73) Assignee: EZ-OFF WEIGHT LOSS, LLC, Leawood, KS (US)

( * ) Notice: Subject to any disclaimer, the term of this patent is extended or adjusted under 35 U.S.C. 154(b) by 388 days.

(21) Appl. No.: 15/724,929

(22) Filed: Oct. 4, 2017

(65) Prior Publication Data

US 2018/0116850 A1    May 3, 2018

Related U.S. Application Data

(60) Provisional application No. 62/403,975, filed on Oct. 4, 2016.

(51) Int. Cl.
  *A61F 2/04* (2013.01)
  *A61F 5/00* (2006.01)
(52) U.S. Cl.
  CPC .......... *A61F 5/0033* (2013.01); *A61F 5/0043* (2013.01); *A61F 5/0076* (2013.01);
  (Continued)
(58) Field of Classification Search
  CPC .... A61F 5/0033; A61F 5/0003; A61F 5/0043; A61F 5/0076; A61F 2002/045;
  (Continued)

(56) References Cited

U.S. PATENT DOCUMENTS 4,315,513 A    2/1982    Nawash et al.
4,356,824 A    11/1982    Vasquez
(Continued)

FOREIGN PATENT DOCUMENTS

WO    WO 2011/004335    1/2011
WO    WO 2015/020977    8/2014
WO    WO 2014/145799    9/2014

OTHER PUBLICATIONS

International Search Report and Written Opinion Corresponding to International Application No. PCT/US2014/030625, Completed Aug. 1, 2014.
(Continued)

*Primary Examiner* — Ophelia A Hawthorne
*Assistant Examiner* — Heather K Barnwell
(74) *Attorney, Agent, or Firm* — Leydig, Voit & Mayer, Ltd.

(57) ABSTRACT

Provided are devices and related methods for weight loss. A size-varying gastric balloon having a passage connected to an elongated sleeve forms a continuous pathway extension so that swallowed food is not absorbed by the body, thereby promoting weight loss. The connection of the sleeve to the gastric balloon avoids the need to directly anchor the proximal sleeve, with the balloon providing that anchoring function. Also provided are gastric balloons having a shape-controllable funnel to provide desired weight loss parameters tailored to the need of an individual and specially configured double lumen sleeves to facilitate controlled nutrition supply to a patient. Methods of deploying any of the devices described herein for weight-loss are also provided.

20 Claims, 7 Drawing Sheets

(52) U.S. Cl.
CPC ............... *A61F 5/003* (2013.01); *A61F 5/004* (2013.01); *A61F 5/0013* (2013.01); *A61F 5/0036* (2013.01); *A61F 2002/045* (2013.01); *A61M 2210/1053* (2013.01)

(58) Field of Classification Search
CPC .................. A61F 5/0036; A61F 5/004; A61M 2210/1053; A61M 2210/106
See application file for complete search history.

(56) References Cited

U.S. PATENT DOCUMENTS

| | | | |
|---|---|---|---|
| 4,668,225 A | 5/1987 | Russo et al. | |
| 5,007,900 A | 4/1991 | Picha et al. | |
| 5,071,405 A | 12/1991 | Piontek et al. | |
| 5,112,310 A | 5/1992 | Grobe | |
| 5,147,316 A | 9/1992 | Castillenti | |
| 5,167,627 A | 12/1992 | Clegg et al. | |
| 5,259,399 A | 11/1993 | Brown | |
| 5,527,280 A | 6/1996 | Goelz | |
| 5,716,347 A | 2/1998 | Gibbs et al. | |
| 5,720,734 A | 2/1998 | Copenhaver et al. | |
| 5,865,816 A | 2/1999 | Quinn | |
| 5,993,473 A | 11/1999 | Chan et al. | |
| 6,030,361 A | 2/2000 | Miyashiro | |
| 6,419,670 B1 | 7/2002 | Dikeman | |
| 6,454,785 B2 | 9/2002 | De Hoyos Garza | |
| 6,551,270 B1 | 4/2003 | Bimbo et al. | |
| 6,907,992 B2 | 6/2005 | McMichael et al. | |
| 6,910,581 B2 | 6/2005 | McMichael et al. | |
| 7,025,791 B2 | 4/2006 | Levine et al. | |
| 7,122,058 B2 | 10/2006 | Levine et al. | |
| 7,220,284 B2 | 5/2007 | Kagan et al. | |
| 7,267,694 B2 | 9/2007 | Levine et al. | |
| 7,314,489 B2 | 1/2008 | McKenna et al. | |
| 7,316,716 B2 | 1/2008 | Egan | |
| 7,329,285 B2 | 2/2008 | Levine et al. | |
| 7,347,875 B2 | 3/2008 | Levine et al. | |
| 7,476,256 B2 | 1/2009 | Meade et al. | |
| 7,563,254 B2 | 7/2009 | Delegge | |
| 7,678,068 B2 | 3/2010 | Levine et al. | |
| 7,682,330 B2 | 3/2010 | Meade et al. | |
| 7,695,446 B2 | 4/2010 | Levine et al. | |
| 7,758,535 B2 | 7/2010 | Levine et al. | |
| 7,766,861 B2 | 8/2010 | Levine et al. | |
| 7,766,973 B2 | 8/2010 | Levine et al. | |
| 7,794,447 B2 | 9/2010 | Dann et al. | |
| 7,806,870 B2 | 10/2010 | Mastri et al. | |
| 7,815,591 B2 | 10/2010 | Levine et al. | |
| 7,819,836 B2 | 10/2010 | Levine et al. | |
| 7,824,368 B2 | 11/2010 | Clem et al. | |
| 7,833,156 B2 | 11/2010 | Williams et al. | |
| 7,833,202 B2 | 11/2010 | Suzuki | |
| 7,837,643 B2 | 11/2010 | Levine et al. | |
| 7,935,073 B2 | 5/2011 | Levine et al. | |
| 7,976,488 B2 | 7/2011 | Levine et al. | |
| 7,981,163 B2 | 7/2011 | Meade et al. | |
| 8,057,420 B2 | 11/2011 | Meade et al. | |
| 8,096,966 B2 | 1/2012 | Levine et al. | |
| 8,097,000 B2 | 1/2012 | Albrecht | |
| 8,109,910 B2 | 2/2012 | Zastawny et al. | |
| 8,109,943 B2 | 2/2012 | Boraiah et al. | |
| 8,137,301 B2 | 3/2012 | Levine et al. | |
| 8,147,454 B2 | 4/2012 | Watanabe et al. | |
| 8,147,561 B2 | 4/2012 | Binmoeller | |
| 8,162,871 B2 | 4/2012 | Levine et al. | |
| 8,182,459 B2 | 5/2012 | Dann et al. | |
| 8,206,456 B2 | 6/2012 | Stack et al. | |
| 8,211,186 B2 | 7/2012 | Belhe et al. | |
| 8,246,617 B2 | 8/2012 | Welt et al. | |
| 8,303,669 B2 | 11/2012 | Meade et al. | |
| 8,430,811 B2 | 4/2013 | Hess et al. | |
| 9,554,932 B2 | 1/2017 | Pattison et al. | |
| 9,833,350 B2 | 12/2017 | Pattison et al. | |
| 10,219,799 B2 | 3/2019 | Pattison et al. | |
| 10,258,372 B2 | 4/2019 | Pattison et al. | |
| 2002/0042607 A1 | 4/2002 | Palmer et al. | |
| 2002/0055757 A1 | 5/2002 | Torre et al. | |
| 2003/0097099 A1 | 5/2003 | Quinn | |
| 2003/0158569 A1 | 8/2003 | Wazne | |
| 2003/0225393 A1 | 12/2003 | McMichael et al. | |
| 2004/0059289 A1 | 3/2004 | Garza | |
| 2005/0240279 A1 | 10/2005 | Kagan et al. | |
| 2005/0267415 A1 | 12/2005 | Jacques | |
| 2006/0009858 A1 | 1/2006 | Levine et al. | |
| 2006/0030872 A1 | 2/2006 | Culbert et al. | |
| 2007/0123840 A1 | 5/2007 | Cox | |
| 2007/0156165 A1 | 7/2007 | Chang et al. | |
| 2007/0225728 A1 | 9/2007 | Stefanchik et al. | |
| 2007/0255257 A1 | 11/2007 | Willis et al. | |
| 2008/0249474 A1 | 10/2008 | Baker | |
| 2009/0204067 A1 | 8/2009 | Abu-Halawa | |
| 2009/0299486 A1 | 12/2009 | Shohat et al. | |
| 2010/0081875 A1 | 4/2010 | Fowler et al. | |
| 2010/0081883 A1 | 4/2010 | Murray et al. | |
| 2010/0152764 A1 | 6/2010 | Merkle | |
| 2010/0249822 A1 | 9/2010 | Nihalani | |
| 2010/0280368 A1 | 11/2010 | Can et al. | |
| 2010/0312047 A1 | 12/2010 | Forsell | |
| 2010/0324375 A1 | 12/2010 | Piskun | |
| 2010/0331756 A1 | 12/2010 | Meade et al. | |
| 2011/0046537 A1 | 2/2011 | Errico et al. | |
| 2011/0082442 A1 | 4/2011 | Solovay et al. | |
| 2011/0106273 A1 | 5/2011 | Belhe et al. | |
| 2011/0160539 A1 | 6/2011 | Robertson | |
| 2011/0245751 A1 | 10/2011 | Hoffmann | |
| 2011/0257580 A1 | 10/2011 | Meade et al. | |
| 2011/0276091 A1 | 11/2011 | Melanson et al. | |
| 2011/0301523 A1 | 12/2011 | Levine et al. | |
| 2011/0307075 A1* | 12/2011 | Sharma .................. | A61F 5/0036 623/23.65 |
| 2012/0029413 A1 | 2/2012 | Meade et al. | |
| 2012/0078174 A1 | 3/2012 | Tai et al. | |
| 2012/0095495 A1 | 4/2012 | Babkes et al. | |
| 2012/0116362 A1 | 5/2012 | Kieturakis | |
| 2012/0132212 A1 | 5/2012 | Nishtala | |
| 2012/0184967 A1 | 7/2012 | Levine et al. | |
| 2012/0203271 A1 | 8/2012 | Larkin et al. | |
| 2012/0215152 A1 | 8/2012 | Levine et al. | |
| 2012/0232339 A1 | 11/2012 | Csiky | |
| 2012/0323081 A1 | 12/2012 | Son | |
| 2013/0012862 A1 | 1/2013 | Meade et al. | |
| 2013/0041231 A1 | 2/2013 | Bonadio et al. | |
| 2013/0041372 A1 | 2/2013 | Welt et al. | |
| 2013/0060091 A1 | 3/2013 | Azarbarzin et al. | |
| 2013/0066304 A1 | 3/2013 | Belson et al. | |
| 2013/0102876 A1 | 4/2013 | Limon et al. | |
| 2013/0211196 A1 | 8/2013 | Belson et al. | |
| 2014/0012178 A1 | 1/2014 | Chin | |
| 2014/0276338 A1* | 9/2014 | Pattison ................ | A61F 5/0079 604/8 |
| 2015/0150699 A1* | 6/2015 | Pattison .................. | A61F 5/003 606/192 |
| 2019/0314009 A1 | 10/2019 | Pattison et al. | |

OTHER PUBLICATIONS

International Search Report and Written Opinion of the International Searching Authority Corresponding to International Application No. PCT/US2014/049639, Completed Nov. 12, 2014.
International Search Report and Written Opinion of the International Searching Authority Corresponding to International Application No. PCT/US2014/067689, Completed Mar. 30, 2015.
International Search Report and Written Opinion of the International Searching Authority Corresponding to International Application No. PCT/US2014/067697, Completed Mar. 30, 2015.
Search Report and Written Opinion, dated Dec. 1, 2017, corresponding to International Application No. PCT/US2017/055121 (filed Oct. 4, 2017), parent of the present application, 17pp.

* cited by examiner

SLEEVE-ANCHORABLE GASTRIC BALLOON FOR WEIGHT LOSS

CROSS-REFERENCE TO RELATED APPLICATIONS

This application claims the benefit of priority of U.S. Provisional Application Ser. No. 62/403,975 filed Oct. 4, 2016, which is hereby incorporated by reference to the extent not inconsistent herewith.

BACKGROUND OF INVENTION

Obesity and related health issues and risks are an increasing problem, especially in the U.S. where more than 1 in 3 adults are considered obese, and more than 1 in 20 adults are considered to have extreme obesity. NIH "Overweight and Obesity Statistics" by NIDDK (October 2012). Obesity and being overweight are risk factors for a number of health problems, including: type 2 diabetes, heart disease, high blood pressure, cancer, nonalcoholic fatty liver disease and various cardiovascular issues. Weight loss treatment, particularly when diet exercise and behavioral therapy fail to achieve desired weight loss, includes, weight-loss drugs and surgery.

Drug use for weight-loss, however, may have only modest success, is prone to unpleasant side-effects and has uncertain long-term safety. Furthermore, patients generally regain lost weight when drug use is discontinued. While surgical treatments generally achieve rapid initial weight loss and attendant health improvements over the longer term, such surgery is expensive, high-risk including and up to mortality, and its benefits may be reduced due to patient behavior and non-compliance with post-surgical dietary restrictions.

Recent effort has focused on achieving the benefit of surgery using minimally invasive procedures that use various medical devices. For example, U.S. Pub. No. 2014/0276338 and PCT Pub. No. WO 2014/145799 (Pattison et al.) describe prosthetic devices for restricting food in the stomach and small intestine with a intragastric displacement balloon and a malabsoprtion sleeve positioned in the small intestine. U.S. Pub. No. 2015/0150699 further improves minimally invasive device characteristics, including by a specially configured balloon having an annulus and improved placement and anchoring procedures. One challenge with the placement of those devices, however, is that the proximal end of the malabsorption sleeve requires separate anchoring to ensure reliable positioning and position maintenance during use.

There is a need in the art, therefore, for an improved weight loss device that further minimizes steps required during surgery, thereby further decreasing cost, surgical effort and complications while maintaining and even improving weight loss. Provided herein are devices and related methods that address this need of a readily and simply deployed weight loss device that has the option of custom-tailoring to the needs of the patient, while maintaining a low risk of complications and adverse side-effects.

SUMMARY OF THE INVENTION

Provided herein are improved weight loss devices and related methods for obesity treatment in a manner that minimizes surgical effort and intervention. The devices and methods are extremely minimally invasive and easily deployed. This is achieved by configuring the elongated sleeve that functions as a malabsorption sleeve and the gastric space-occupying balloon in a manner that avoids the need for separate anchoring of the proximal sleeve end. Instead, the sleeve proximal end is connected to the gastric balloon so that the proximal anchoring occurs with anchoring of the gastric balloon. In this manner, the separate anchor of the proximal end of the sleeve is avoided, thereby increasing ease of deployment and reliability during use and decreasing complications.

Any of the devices provided herein may have a controllable geometry, such as gastric balloon funnel shape and size, to improve and tailor weight loss outcomes and treatment. This is achieved by a specially designed funnel shape to control the amount of food introduced to the device via a balloon passage and that bypasses the stomach, and also to reduce risk of occlusion by swallowed food. The device may be tailored to a desired treatment, such as rate of weight loss, by varying the shape of the funnel. In this manner, there is control of the relative amount of food that enters the elongated sleeve via the gastric balloon passage compared to food that enters the stomach lumen not occupied by the balloon and that may subsequently provide nutrients for absorption by the intestines and associated caloric gain.

The devices and methods provided herein may be employed with a transabdominal gastric cannula device, including any of those described in US Pub. Nos. 2015/0038794 and 2015/0150595, which are hereby specifically incorporated by reference for the devices and methods described therein, including for use in inserting, manipulating and/or anchoring any of the devices described herein. Similarly, the balloon and sleeve may have any one or more characteristics as described in US Pub. Nos. 2014/0276338 and 2015/0150699.

Provided herein are weight-loss devices for treatment of obesity in a patient. The device may comprise a gastric balloon configured for positioning in a stomach lumen. The gastric balloon has a gastric balloon surface that defines an interior of the balloon which is inflatable to provide a volume adjustable balloon. The balloon surface has a proximal end and a distal end with a passage spanning between the proximal end and the distal end. During use, the passage substantially aligns in a direction from the lower esophageal sphincter toward a pyloric sphincter with the gastric balloon proximal end facing the lower esophageal sphincter and the gastric balloon distal end with attached non-deployed small bowel sleeve (e.g., elongated sleeve in a stored configuration) facing the pyloric sphincter. In this manner, swallowed food can enter the balloon passage at the proximal end and, under normal stomach motility, be forced toward and out of the passage distal end. To position the balloon in the stomach, one or more gastric balloon anchors are connected to or extending from the gastric balloon surface. Those anchors may be used to reliably position the gastric balloon in a stomach lumen during use, such as by directly or indirectly connecting the balloon to a stomach wall or to a cannula that passes through the stomach wall.

The device may further have an elongated sleeve, also referred herein as a "malabsorption sleeve", connected to the gastric balloon and configured for insertion into at least a portion of a patient's small intestine during use. The elongated sleeve may further comprise an additional sleeve so as to provide a double-lumen sleeve. The elongated sleeve may further comprise a sleeve wall having an inner-facing surface that forms a sleeve lumen, wherein the sleeve lumen extends from a sleeve proximal end to a sleeve distal end. The sleeve proximal end is connected to the gastric balloon distal end to provide a continuous pathway extension of the gastric balloon passage and the sleeve distal end is configured to be positioned during use at a mid to distal region of the small intestine. Depending on the application of interest, the total length of the sleeve may correspond to anywhere between about 10%-15% through to about 50%-70% of the length of the small intestine. The total length of the sleeve may correspond to about 50 cm to 500 cm, or about 200 cm to 300 cm. In this manner, food that enters the gastric passage and the proximal passage end is forced out of the distal end of the gastric passage and into the sleeve lumen, where it is maintained in physically separated position from the small intestine by the sleeve wall. The physical properties of the sleeve wall, including permeability and/or selective permeability, are selected to ensure the caloric intake of the patient is reduced, even for large quantities of ingested food, in such a manner so as to promote weight loss. Accordingly, the sleeve lumen may be impermeable such that no to minimal nutrients are passed out of the sleeve lumen to the space between the intestinal wall and the outer facing surface of the sleeve wall. Alternatively, for applications where some nutrient exchange is desired, the sleeve wall may be semi-permeable, with the permeability adjusted by selection of the sleeve wall properties. For example, the sleeve wall may comprise a polymer having a selected porosity, including of select pore size and percentage of wall surface area occupied by pores, such as average pore diameters from one to several microns, such as 1 µm to 10 µm and pore density of 1% to 10%. In a double lumen configuration, the inner sleeve may be non-permeable and the outer sleeve may be permeable to nutrients introduced to the second lumen so as to ensure adequate nutrient uptake by the patient.

The continuous pathway extension of the passage by the sleeve lumen may be configured to prevent unwanted leakage of ingested food out of the passage to a surrounding gastric lumen, specifically the stomach space surrounding the device, without adversely affecting normal gastric secretion to the small intestine during use, including gastric emptying. For example, some space may be provided between the sleeve wall and the pyloric sphincter to facilitate normal gastric emptying.

The elongated sleeve connection to the gastric balloon distal end may be a continuous extension of the gastric balloon distal end. Alternatively, the elongated sleeve may be formed of a component distinct from the gastric balloon, and the elongated sleeve connected to the gastric balloon by a connection means. Examples include, but are not limited to, one or more of: an adhesive, a fastener, staples, sutures, a geometric tight fit, or a threaded connector.

The elongated sleeve may comprise a double lumen, the double lumen formed by an inner elongated sleeve positioned within an outer elongated sleeve. The inner elongated sleeve is configured to contain the food that has passed through the gastric passage. The outer, or second, lumen, formed by an inner-facing wall of the outer sleeve and an outer-facing wall of the inner sleeve, may provide a platform by which nutrients are introduced to the patient, either ingested by the patient or provided via a conduit that terminates in the outer lumen. Accordingly, the inner elongated sleeve may be impermeable and the outer elongated sleeve permeable to desired nutrients.

Each of the inner and outer sleeve proximal ends may be connected to the gastric balloon distal end.

The double lumen can also be beneficial by enhancing a mechanical stiffness of the elongated sleeve to avoid unwanted sleeve twisting excessive torque, kinking, invagination or proximal migration during deployment and use. The second lumen may also extend to the exterior surface of the gastric balloon from the distal end of the balloon towards the proximal end of the balloon in one or more conduit's and terminating at a separate injectable port at the proximal end of the balloon that can be easily accessed via the endoscope to provide the patient needed nutrients vitamins minerals and other materials as necessary. These provided materials can travel the extent of this double-lumen with permeable external wall on the exterior surface of the gastric balloon into the second lumen of the double lumen elongated sleeve (e.g., the small bowel sleeve) and these materials can exit the second lumen's external permeable wall and thus can be absorbed by the small intestine.

The gastric balloon surface proximal end and passage proximal end can be formed into a shape corresponding to a funnel and having a pouch volume, with the passage proximal end within a bottom region of the funnel. In this manner, the funnel may provide a type of holding chamber for food that has been swallowed by the patient but has not passed into the passage. This pouch created by the funnel proximal end of the gastric balloon is somewhat analogous to a surgical gastric pouch performed by the traditional gastric bypass surgery. Although the pouch provided herein has the additional advantage of size and volume adjustability, as well as having its connection size and/or luminal distance also adjustable as food passes into the gastric passageway via an adjustable prosthetic anastomosis. The ability to adjust the gastric pouch size as well as the size of the passageway from the pouch into the gastric passageway is a significant advantage over surgical gastric bypass which were left with a fixed surgical result. The geometry of the surgical gastric bypass can only be changed with extensive surgical manipulation.

The funnel may be described in terms of a variety of physical parameters, such as a funnel angle of between 15° and 165° and/or a pouch volume of between 30 mL and 300 mL.

The funnel physical parameters may be user-adjustable, including by having its own separate inflation port to control funnel volume and angle as well as to control the size of the connection from the pouch to the gastric balloon passage or the prosthetic anastomosis, so as to provide the ability to control rate of weight loss. For example, the funnel pouch volume may be user-adjustable, with smaller funnel pouch volumes and wider funnel angles allowing for increased leakage of swallowed food around the gastric balloon and not into the passage, thereby decreasing weight loss in the event the rate of weight loss is undesirably high. Similarly, if the rate of weight loss is desirably higher, the pouch volume may be increased, with a corresponding increase in rate of weight loss as more swallowed food is collected into the gastric balloon passage, thereby bypassing absorption by the small intestine.

A funnel fluid port operably connected to the gastric balloon surface proximal end can provide the ability for a user-controlled pressure and volume to the gastric balloon surface proximal end and thereby control a shape and volume of the funnel.

The funnel shape and volume can be adjusted to achieve a desired rate of weight loss in a patient by varying an amount of swallowed food that bypasses the gastric balloon passage, with smaller funnel pouch volume allowing more food to bypass and larger funnel pouch volume allowing less food to bypass.

The funnel shape and volume adjustment provides for a controlled percentage of swallowed food that enters the gastric balloon passage that ranges from 5%-15% to 80%-95% of swallowed food, and any range desired therebetween.

A gastric balloon fluid port may be connected to an interior volume of the gastric balloon, so that the gastric balloon fluid port provides a pressurization and volume control of the gastric balloon that is independent of the funnel shape and volume control by said funnel fluid port. The pressurization may be provided by a fluid conduit that is connected to the fluid port, for introducing and removing fluid, as desired. The fluid may be a gas or may be a liquid. This separate fluid port can increase or decrease the volume of the gastric balloon as well as increase or decrease the diameter of the gastric balloon passage traversing the gastric balloon.

The funnel during use results in less than a user-selected amount of swallowed food that bypasses gastric balloon passage, such as about 50% or less of swallowed food that does not enter the gastric balloon passage.

The device is configured to position the gastric balloon surface proximal end from between 1 cm and 5 cm from a gastro-esophageal junction (e.g., lower esophageal-gastric sphincter) and the gastric balloon surface distal end from between 1 cm and 5 cm from a gastro-intestinal junction (e.g. pyloric sphincter).

The passage may itself be funnel-shaped, with a larger diameter toward the proximal entry end and a smaller diameter toward the distal end, to reduce a risk of occlusion. The passage may be quantitatively described as having one or more of: a maximum diameter toward the proximal end that is greater than or equal to 2 cm and less than or equal to 7 cm; a minimum diameter toward the distal end that is greater than or equal to 0.5 cm and less than 2 cm; and/or a funnel length that is greater than or equal to 1 cm and less than or equal to 50 cm. The term "toward" refers to the beginning 10% of the passage for the proximal end and the last 10% of the passage for the distal end, including at the proximal and distal ends, respectively.

The gastric balloon passage may be described as having an adjustable average diameter, with an average passage diameter adjustable from a minimum of 0.5 cm to a maximum of 4 cm, including via pressurization of the balloon interior, such as via the balloon fluid port and introduced/removed fluid.

The elongated sleeve, as desired, may have a stored and a deployed configuration, with the stored configuration assisting with placement of the device with a minimally invasive intervention. Accordingly, the device may be described as having the elongated sleeve in a stored configuration adjacent to the gastric balloon surface distal end. The stored configuration may be provided by the elongated sleeve that is in a coiled, rolled or folded configuration. For example, a storage element connected to the gastric balloon surface and in operable connection with the elongated sleeve may store the elongated sleeve adjacent to the gastric balloon surface distal end. Examples of storage elements include, but are not limited to, a removable suture, a removable clip, staple or other removable fasteners. These removable fasteners can extend from the inside of the distal gastric balloon passage around the folded sleeve and connect externally in the area of the distal gastric balloon surface. Thus the fastener can easily be removed with the use of flexible endoscopy or other appropriate instrumentation on a scope, as the scope passes through the distal gastric balloon passage prior to sleeve deployment.

The suture may be configured to release the elongated sleeve by an endoscope that traverses the gastric balloon passage or through a transabdominal gastric opening and configured to release or remove the suture from its external aspect to provide the ability to deploy the elongated sleeve into a deployed configuration. The endoscope may have cutters or graspers to cut or remove the suture, for example.

The elongated sleeve may be configured to operably connect with the endoscope during insertion of the device so as to deploy the elongated sleeve in the small intestine by a distally-directed movement of said endoscope relative to said gastric balloon. For example, the endoscope may grasp a distal end of the sleeve and move into the small intestine in a distal direction away from the stomach and place a sleeve anchor at a desired location, or otherwise connect the distal sleeve end to the intestine wall. Deployment of a double lumen elongated sleeve and various aspects related thereto are described in US Pub. Nos. 2014/0276338 and 2015/0150699, which are hereby specifically incorporated by reference to the extent not inconsistent herewith.

The device may have a stored configuration that corresponds to the elongated sleeve that is within 5 mm of the gastric balloon distal end and the deployed configuration corresponds to a sleeve length between said sleeve distal and proximal ends that is between 50 cm and 500 cm. In other words, the stored configuration corresponds to the proximal and distal ends of the sleeve that may be within a stored distance, such as a stored distance that is less than about 2 cm, less than 1 cm, or less than 5 mm. In contrast, in the deployed configuration, the sleeve may be extended to full length, with a maximum separation distance between the distal and proximal ends between about 50 cm and 500 cm. Deployment and anchoring of the distal end of the elongated sleeve and various embodiments are further described in US Pub. Nos. 2014/0276338 and 2015/0150699, which are specifically incorporated by reference.

A distal sleeve anchor may be connected to the sleeve distal end, or a region adjacent thereto, for anchoring the sleeve distal end to the distal region of the small intestine during use. In this context, "distal region" simply refers to a downstream region of the small intestine, such as between about 50 cm and 500 cm from the pyloric sphincter.

The device may also be described as having a no-anchor region to further emphasize the distinction of the instant device compared to conventional malabsorption sleeves that have a plurality of longitudinally separated anchors, with one to anchor the proximal sleeve end and another to anchor the distal sleeve in end. The instant devices, in contrast, only need anchors at the distal sleeve end as the proximal end that is connected to the gastric balloon avoids the need for a separate proximal sleeve anchor. Accordingly, the no anchor region extends from the distal end of the balloon to the distal sleeve anchor.

Any of the devices may have a proximal sleeve end connected to the distal gastric balloon end to provide anchoring of the proximal sleeve portion for reliable positioning of the sleeve proximal end during use without a proximal sleeve anchor.

The devices provided herein may be used with a transabdominal gastric cannula, including any of those described in US Pub. No. 2015/0150595 and 2015/0038794, passing through a stomach wall, wherein the gastric balloon anchor is connected to the transabdominal gastric cannula or a wall of the stomach to position the gastric balloon in the stomach during use.

The device may further comprise a first port in the transabdominal gastric cannula to accommodate a conduit for introducing and/or removing fluid to vary a volume of the gastric balloon during use. The conduit for introducing and/or removing fluid may convey a gas or a liquid to/from a gastric balloon lumen formed by the gastric balloon surface, thereby expanding/contracting the balloon volume and gastric passageway diameter as well as a second port to adjust the gastric funnel at the proximal end of the gastric balloon thereby providing geometric control and variation of the funnel, including the funnel volume and size at the proximal end..

The device may further comprise a third port configured to accommodate a sleeve conduit for introducing nutrients to the small intestine during use of the device, including to a second lumen of a double lumen configuration that is formed by the elongated sleeve outer-facing wall and an outer-positioned sleeve inner-facing wall that faces the elongated sleeve outer-facing wall. This second lumen of the elongated sleeve allows for nutrient and vitamin absorption and can extend past the junction of the sleeve and the gastric balloon and further extend along the outer surface of the gastric balloon to its proximal aspect, terminating at a third infusion port.

The device may comprise a plurality of balloon anchors numbering between 3 and 7 for anchoring the balloon to the gastric wall.

During use the gastric balloon and passage together may have a volume that occupies at least 50% to 90% of a lumen volume of the stomach when inflated, thereby providing a feeling of satiety to the patient. If fully deflated and anchored, the volume occupied may be about 10% to 20%.

Also provided herein are methods of deploying any of the devices described herein for weight loss treatment in a patient. For example, the method may comprise the steps of: providing a device comprising a gastric balloon having a passage extending there-through connected to an elongated sleeve, wherein the elongated sleeve is in a stored configuration adjacent to a surface of the gastric balloon. Adjacent may refer to the maximum distance of the stored sleeve from the gastric balloon surface that is within 2 cm, 1 cm or 5 mm. The device can be introduce endoscopically or laparoscopically via a transabdominal gastric cannula to a stomach lumen and positioning a proximal end of the gastric balloon having a funnel shape opening to face an esophageal sphincter. The distal end of said gastric balloon is positioned to face a pyloric sphincter. The gastric balloon is anchored to a wall of the stomach lumen, thereby aligning the passage in a direction from the esophageal sphincter to the pyloric sphincter. In this manner, the passage is able to accommodate swallowed food and force the food through the passage from the proximal passage end, to the distal passage end, and out to the elongated sleeve. A storage element is severed to release a distal end of the elongated sleeve from the gastric balloon followed by positioning of the sleeve distal end to a desired distal location in a small intestine. To ensure the distal end of the elongated sleeve is properly positioned, the sleeve distal end is anchored at the desired distal location and the weight loss device is thereby deployed. As discussed, the device configuration allows for significantly easier and safer implantation as there is no need to separately manipulate and anchor a proximal sleeve anchor.

The method may further comprise the steps of: inserting a transabdominal gastric system to the stomach lumen through a transabdominal wall of the patient to form a working channel; inserting the weight loss device through the working channel; and anchoring the balloon to the transabdominal gastric system and/or to a stomach wall.

The severing step may comprise: contacting a medical device having severing means to the storage element, either on the internal aspect or the external aspect; and actuating the severing means to physically cut said storage element. The medical device may be an endoscope with an actuator that activates a cutter to cut the storage element, or a grasper to pull out the storage element.

Also provided herein are gastric balloons for obesity treatment. The balloon has a gastric balloon surface with a proximal end and a distal end forming a gastric balloon volume. A passage traverses from the proximal end to the distal end. A shape-adjustable funnel is formed at, or connected to, the gastric balloon surface proximal end that provides a pouch volume at a proximal end of the passage configured during use to collect swallowed food and direct swallowed food toward the passage. A gastric balloon fluid port is operably connected to the gastric balloon surface for introducing or removing a fluid to adjust the gastric balloon volume. A funnel fluid port is operably connected to the shape-adjustable funnel for introducing or removing a fluid to adjust a shape and volume of the funnel, wherein the shape adjustment is independent of the gastric balloon volume.

The gastric balloon may further comprise an elongated sleeve having a sleeve proximal end and a sleeve distal end, wherein the sleeve proximal end is connected to the gastric balloon surface distal end to provide a continuous pathway extension from the passage distal end. A sleeve anchor may be connected to the sleeve distal end configured to anchor the sleeve distal end to the distal region of a small intestine during use.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

DETAILED DESCRIPTION OF THE INVENTION

In general, the terms and phrases used herein have their art-recognized meaning, which can be found by reference to standard texts, journal references and contexts known to those skilled in the art. The following definitions are provided to clarify their specific use in the context of the invention.

"Balloon" refers to a gastric space-occupying balloon that can be inserted into the stomach and inflated to provide a feeling of satiety to the patient. Furthermore, the balloon is specially designed to have a passage through which food may pass from a proximal end that faces the esophageal region to a distal end that faces the pyloric sphincter. The advantage with such a passage is the combination of the malabsorption or elongated sleeve that extends from the distal end of the balloon, through the pyloric sphincter, and along a significant portion of the small intestine, toward the large intestine. In this manner, even if the patient continues to overeat after balloon placement, those calories associated with the swallowed food are not absorbed by the body because of the elongation sleeve. Furthermore, the anchoring of the sleeve to the balloon in a manner to form a continuous pathway extension significantly reduces surgical effort, with an "automatic" proximal sleeve anchoring upon balloon anchoring. This saves time and effort, while also further decreasing complications.

"Sleeve" refers to a biocompatible material having a lumen through which food that has traversed the balloon passage may pass. An "elongated sleeve" simply refers to a sleeve that is extended to traverse a desired longitudinal distance along a small intestine, wherein the sleeve is inserted in the small intestine lumen. The sleeve may be constructed of a material that does not allow the passage of nutrients from the sleeve lumen to the small intestine wall. Accordingly, elongated sleeve may be used interchangeable with "malabsorption" sleeve.

"Proximal" generally refers to the end of a component that is closest toward the esophagus. "Distal", therefore, generally refers to the end of a component that is furthest from the esophagus and, correspondingly, closest to the end of the small intestine.

"Continuous pathway extension" refers to a lumen that formed from the combination of the balloon passage and elongated sleeve lumen. This is the pathway that swallowed food introduced to the balloon passage may take, but need not be limited to a completely impermeable path. For example, the portion of the sleeve that connects to and is in the vicinity of the gastric balloon and in contact with the gastric environment, may have openings, pores, or other passages to allow the exchange of certain fluids and other desirable biological components in the gastric environment. Such configuration is accommodated by the devices provided herein so long as there is not an undue adverse impact on desired weight-loss.

Example 1

Sleeve-Anchorable Gastric Balloon

Figure 1:
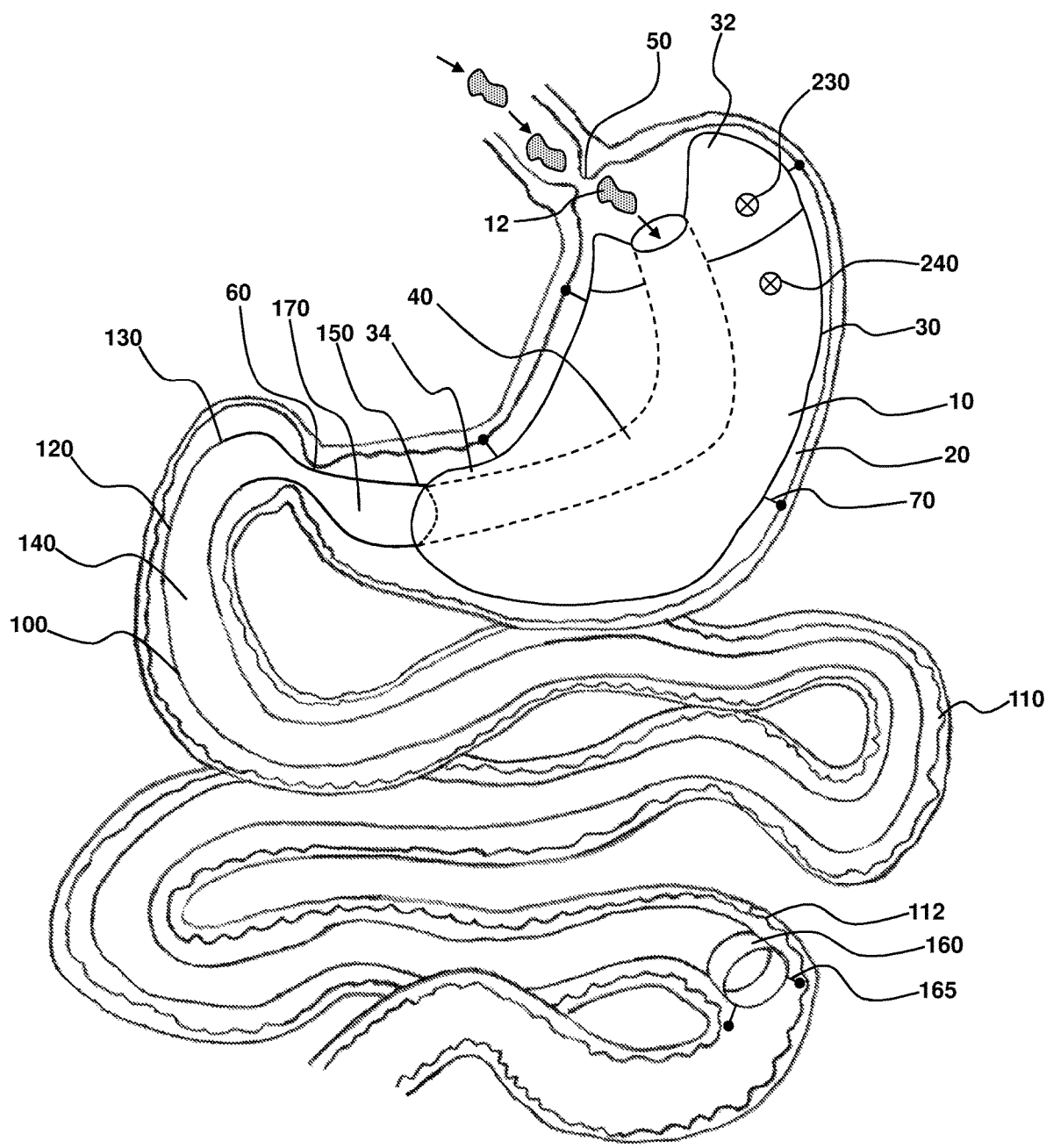
FIG. 1 is a schematic illustration of a gastric volume occupying balloon with a malabsorption elongated sleeve extending therefrom and extending through the small intestine to facilitate weight loss. In this illustration, the gastric passageway is eccentrically placed to mimic that of a sleeve gastroplasty with one aspect of the proximal end of the balloon filling the gastric fundus to accomplish early satiety and weight loss.

FIG. 1 illustrates a weight loss device for treatment of obesity in a patient formed with a gastric balloon 10 that is positioned in a stomach lumen 20. That gastric balloon has a gastric balloon surface 30 with a proximal end 32 and a distal end 34. Proximal end refers to the portion of the balloon surface that faces toward the esophageal sphincter 50 and the distal end the portion of the balloon surface that faces toward the pyloric sphincter 60. Such a positioning of the distal and proximal ends of the balloon surface aligns a gastric balloon passage 40 that substantially aligns in direction from the esophageal sphincter 50 to the pyloric sphincter 60. "Substantially aligns" in this aspect refers to the functional ability of the passage to direct ingested food 12 that passes the esophagus into the stomach directly toward the pyloric sphincter without substantial blockages or other unwanted obstructions during use. The substantial alignment reflects that it is not feasible or practical to introduce and maintain one exact alignment of the passage, but that depending on gastric conditions and balloon inflation pressure and volume, there is toleration in the passage alignment with the direction formed between the sphincters without an undue sacrifice in device performance characteristics such as blockages or food passage bypass.

To ensure the balloon maintains proper positioning within the gastric lumen, a plurality of gastric balloon anchors 70 may connect the balloon surface to the stomach wall during use.

An elongated sleeve 100 is connected to the gastric balloon distal end is configured for insertion into at least a portion of the patient's small intestine 110 during use. The elongated sleeve has a sleeve wall 120 with an inner facing surface 130 that forms a sleeve lumen 140 that extends from a sleeve proximal end 150 to a sleeve distal end 160. The sleeve proximal end 150 is connected to the gastric balloon distal end 34 with the sleeve lumen 140 operably connected to the gastric passage 40 to form a continuous pathway extension between 40 and 140 and to anchor a proximal sleeve portion 170. "Continuous pathway extension" refers to the ability to direct food from the gastric balloon passage to the small intestine via the sleeve lumen, without unwanted leakage out of the balloon distal end. The continuous pathway extension may accommodate openings, pores or other gaps so long as there is not an adverse impact on a desired weight loss treatment or the ability to reliably anchor the proximal end of the sleeve to the balloon without extraneous anchor elements connected to the sleeve proximal end.

The sleeve distal end 160 is configured to be reliably positioned during use at a distal region 112 of the small intestine 110 during use, including by one or more anchors 165 that provide a connection between sleeve distal end and the small intestine at a desired distal region.

Figure 2:
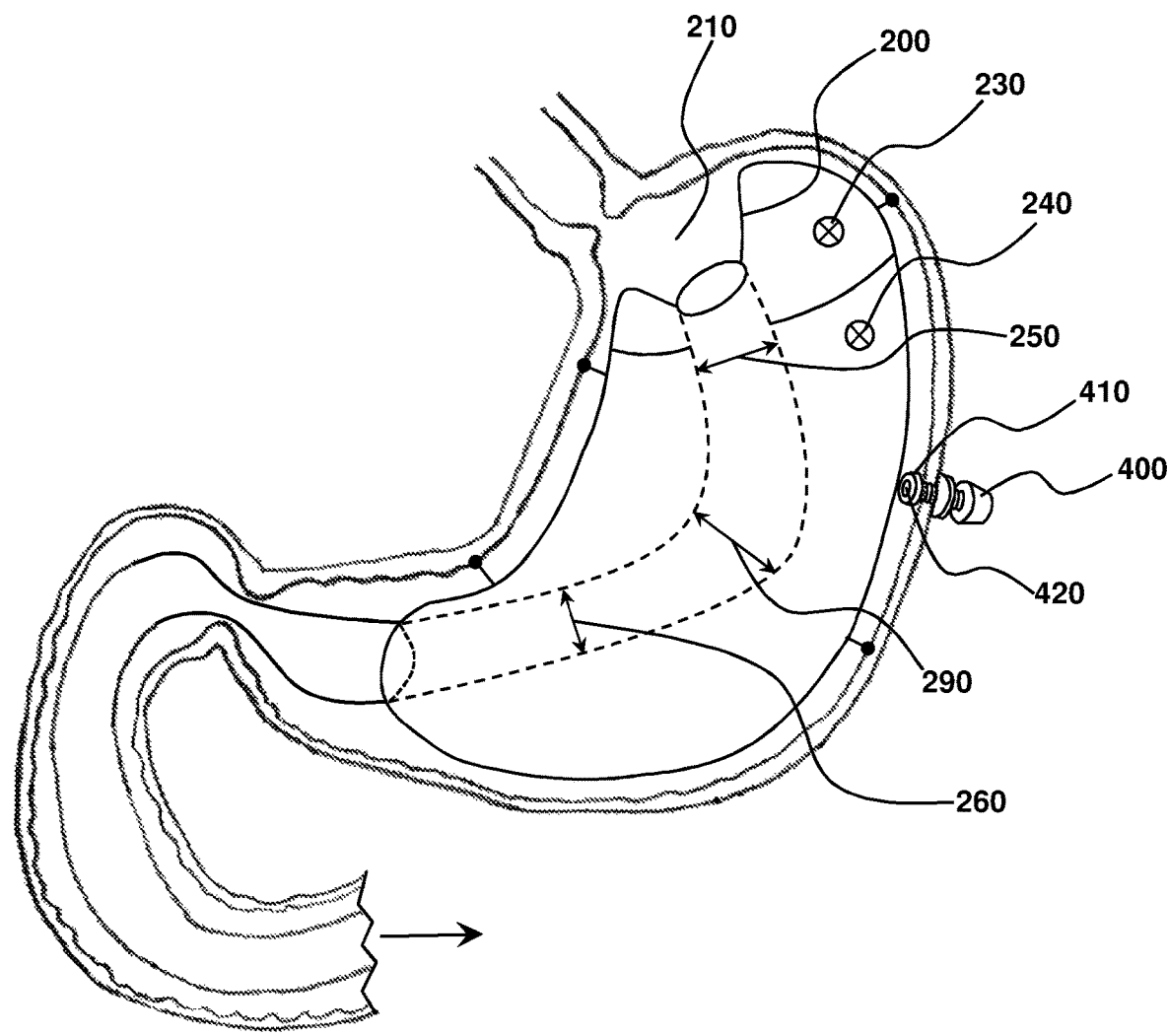
FIG. 2 illustrates a transabdominal gastric cannula with the weight loss device of FIG. 1.
Figure 6:
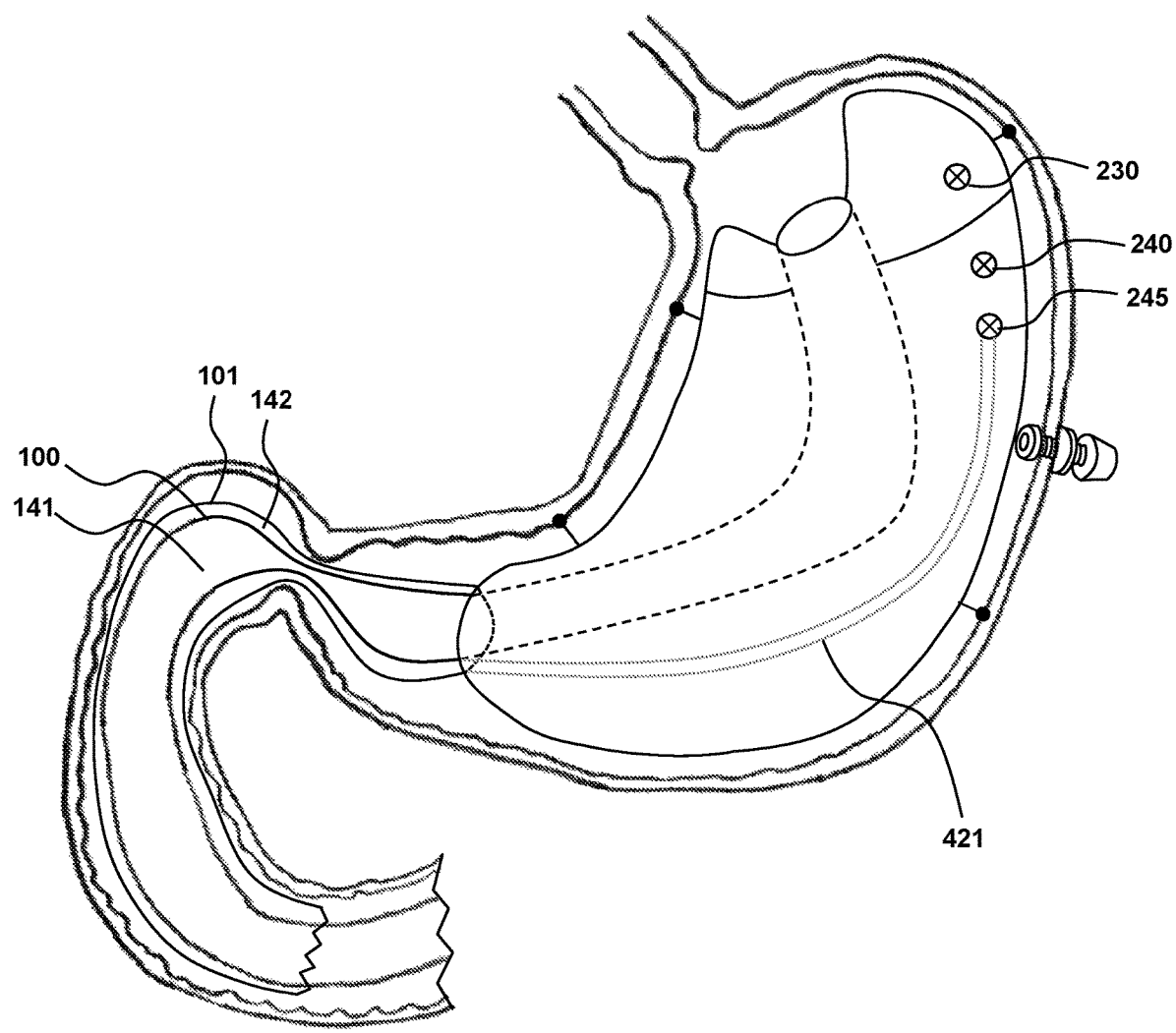
FIG. 6 schematically illustrates an elongated sleeve having a double lumen with a fluid conduit for introducing nutrients to the lumen formed between the sidewalls of the two sleeves extending from the transabdominal gastric cannula. In this manner, nutritional elements, including vitamins and minerals, may be introduced at a third port and provided to the second lumen of the double lumen elongated sleeve for subsequent absorption by the small intestine.

FIG. 2 illustrates various physical parameters and geometry of the gastric balloon. For example, a funnel 200 may be formed from the gastric balloon proximal end, with the funnel having a funnel volume 210 and a funnel angle and funnel distance. The gastric balloon passage may have a shape-varying lumen, such as an effective diameter defined as by the cross-sectional area at a specific position along the passage ($A=\pi D^2/4$). The passage may have a variety of configurations, shapes, and physical dimensions depending on the application of interest. For example, as desired a maximum diameter 250 may be positioned toward the proximal end, a minimum passage diameter 260 toward the distal balloon end, and an average diameter 290, including an adjustable average diameter that may depend, for example, on the amount of pressure generated by a fluid introduced to the gastric balloon lumen portion via port 240 and/or funnel port 230. As illustrated in FIG. 6, a third port (also referred herein as second lumen fluid port) 245 may fluidically connect to the second lumen via second lumen fluid conduit 421, thereby providing ready access for provision of vitamins, nutrients, minerals and other caloric requirements to the patient to maintain good patient health. Conduit 421 may feed the second lumen for the double lumen configuration, or feed directly to the small intestine surrounding the elongated sleeve in a single sleeve configuration.

Gastric balloon fluid ports 230 240 may provide access to independently inflate the funnel region and the remainder of the gastric balloon, respectively. In this manner, the funnel shape, including funnel volume, may be independently controlled to provide controllable food leakage and attendant weight loss characteristic. The device is compatible with an introduced fluid introduced that is a gas or a liquid. The fluid may be controllably introduced or removed with a fluid conduit introduced endoscopically introduced via the esophagus or laparoscopically through the abdominal wall, including with a transabdominal gastric cannula 400 illustrated in FIG. 2. the cannula 400 may have a first port 410 through which a fluid conduit may fluidically connect to ports 230 and/or 240. A second port 420 may accommodate a sleeve conduit 421 (FIG. 6) for introducing nutrients to the space between the elongated sleeve and small intestine for controlled delivery of nutrients to the patient.

Example 2

Stored and Deployed Elongated Sleeve

Figure 3:
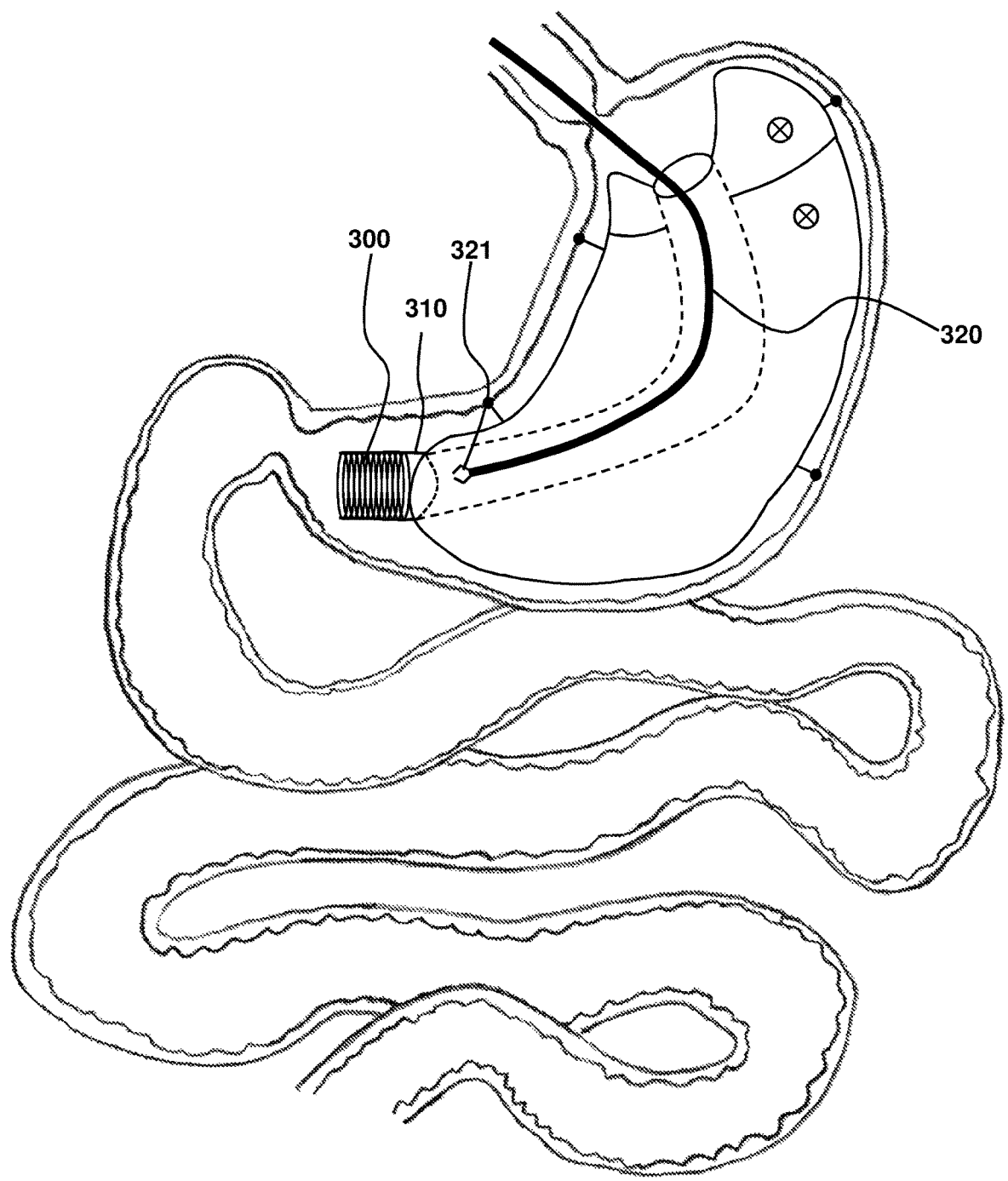
FIG. 3 schematically illustrates the weight loss device of claim 1 with the elongated sleeve in a stored configuration and ready for deployment with an endoscope.
Figure 4:
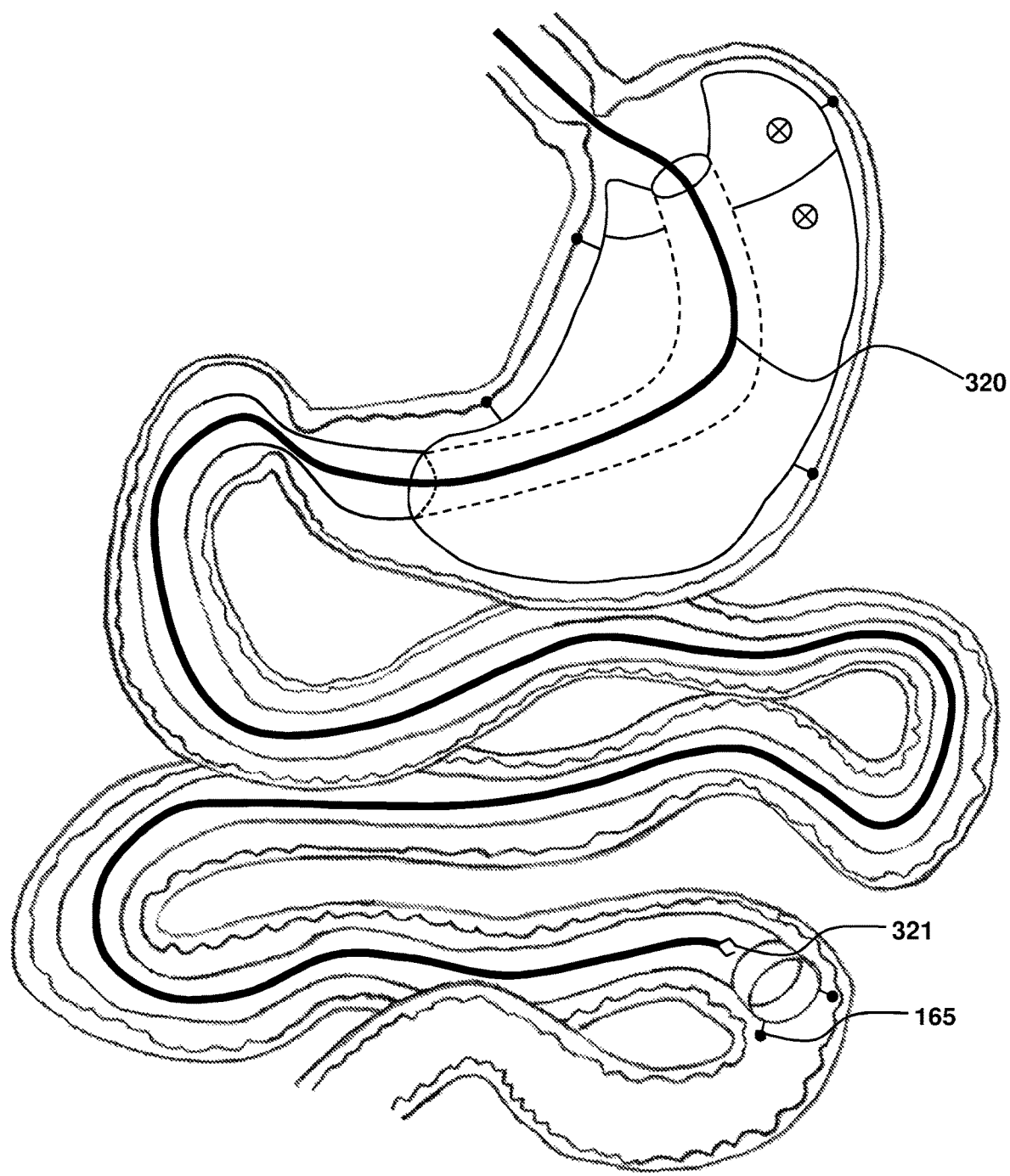
FIG. 4 illustrates positioning of the elongated sleeve distal end with an endoscope that anchors the distal end to a distal region of the small intestine, thereby providing a deployed configuration.

An advantage over the systems provided herein is the ability to easily deploy the system, with fewer surgical manipulations as the design provides a built-in anchoring of the proximal end of the elongated sleeve. FIG. 3 illustrates the device with the elongated sleeve 100 (FIG. 1) in a stored configuration 300. Storage element 310 connected to any gastric balloon surface holds the elongated sleeve in the stored configuration, including in any of a rolled-up or accordion-style folded configuration, such as by a suture that may extend from an internal aspect such as extending from the distal balloon passage, to an external aspect, such as to the distal gastric balloon surface. During insertion, an endoscope 320 may be used to release or remove the storage element, thereby freeing the elongated sleeve distal end from the gastric balloon surface via cutting or removing the storage fastener from the inside aspect of the storage element with a severing means 321 at a distal location of a flexible endoscope 320. In addition this element can be loosened or removed externally if instruments are placed via the external gastric port. FIG. 4 illustrates the endoscope 320 traversing the balloon passage and elongated sleeve lumen (e.g., along the continuous path extension) to position the distal sleeve end at a desired location by a distally-directed movement of the endoscope relative to the gastric balloon. The connection between the elongated sleeve proximal end and the gastric balloon distal surface provides an inherent anchor point that ensures the proximal sleeve end is anchored without having to independently anchor the proximal sleeve end. This significantly increases ease of deployment and reduces surgical intervention time and effort. In addition, this mechanism allows for less surgical complications since there is no need for a paroxysmal sleeve anchor device other than the anchored gastric balloon itself. Anchors 165 that can be deployed or engaged by the endoscope reliably position the distal end of the elongated sleeve. In this manner, there is a no anchor region for the elongated sleeve that extends between the distal sleeve end and balloon. This also reflects that the proximal sleeve end does not have a separate anchor, but instead is inherently anchored to the gastric balloon. This may also be expressed as the proximal 95%, 97% or 99% or more of the sleeve length that is anchor free, with only the very distal end having a separate anchor point.

Example 3

Shape-Adjustable Funnel

Figure 5A:
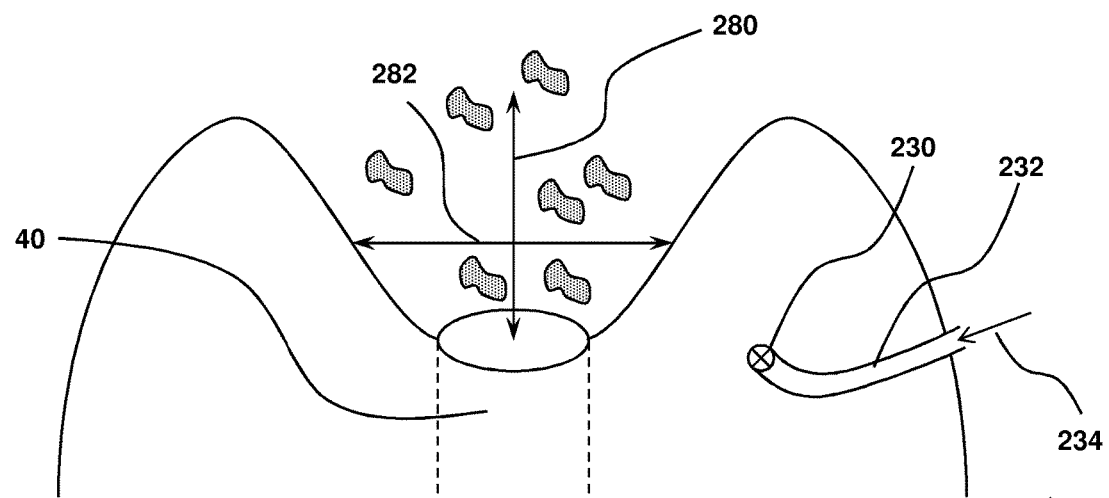
FIGS. 5A and 5B illustrate adjustability of the funnel shape and volume to control the amount of food bypass around the gastric balloon and elongated sleeve, with 5A a more pronounced and larger funnel volume, having a more distinct and circumscribed smaller funnel angle and size compared to 5B having a larger funnel angle and resulting in less funnel volume that passes relatively less food to the gastric balloon passage compared to 5A, as indicated by the arrows for the swallowed food away from the gastric balloon passage. In this manner, FIG. 5A promotes more rapid weight loss and FIG. 5B less rapid weight loss.

To provide an independent control of rate of weight-loss and feeling full or early satiety, the funnel portion of the gastric balloon may be shape-adjustable. Any of a variety of mechanisms may be used to control the shape of the funnel, such as by tensioners or deforming elements. In the illustrated example in FIG. 5A, fluid conduit 232 is connected to funnel fluid port 230 and a fluid introduced to controllably pressurize the funnel portion of the gastric balloon, as indicated by arrow 234 indicating direction of fluid flow. In this manner, the funnel may have a funnel volume defined, in part, by a funnel depth 280 and an average funnel width or diameter 282. FIG. 5A, for example, may correspond to a fully pressurized funnel having a small funnel angle and corresponding larger and well-defined funnel volume, compared to that illustrated in FIG. 5B. Such a relatively larger and well-defined funnel volume increases the amount of ingested food that passes into the gastric passage 40. This increased amount of food will enter the funnel and the gastric balloon passage and will then enter the lumen defined by a non-permeable elongated sleeve wall and result in increased weight loss in FIG. 5A compared to that of FIG. 5B. Of course, the devices and methods provided herein provide a fundamental improvement in the art by providing the ability to control geometry, thereby providing individualized treatment to the patient, irrespective of exact geometries. The devices and methods are compatible with any number of geometries, sizes, shapes and volumes, so long as the desired rate of weight loss is achieved and maintained.

Figure 5B:
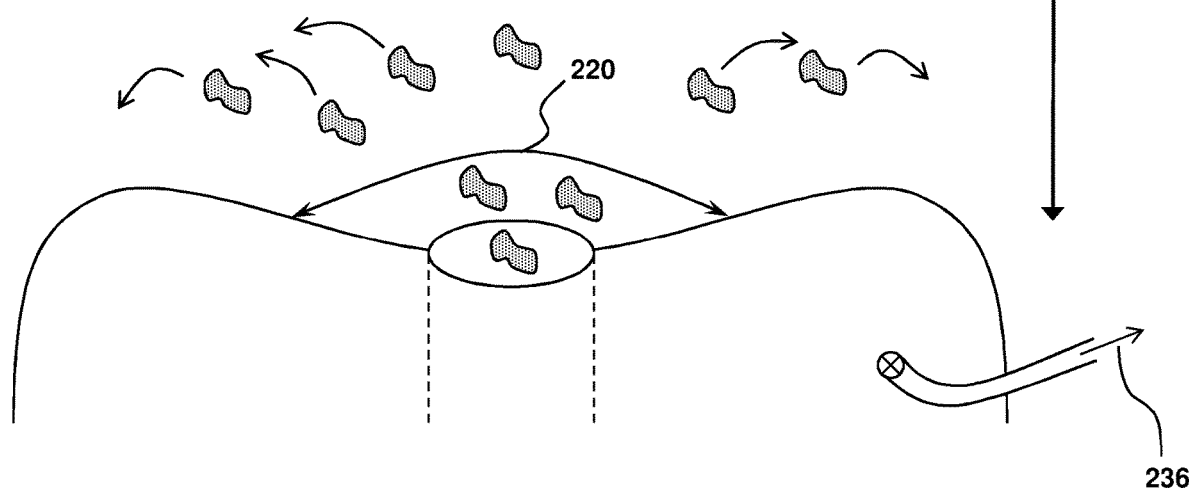

The funnel shape, as illustrated in FIG. 5B, can be varied to increase or decrease the funnel volume, such as by increasing or decreasing the funnel angle 220. This can be achieved by changing the pressure and volume in the funnel region by removal of fluid out of or into port 230 as indicated by arrows 234 and 236. Arrow 238 illustrates the ability to change funnel characteristics to control rate of weight loss. If weight loss is too high, the funnel shape may be changed from FIG. 5A to FIG. 5B by changing and adjusting the desired amount of fluid. In this manner, the amount of food bypassing the funnel 40 may be controlled, with an attendant control of weight loss.

Example 4

Double Lumen Elongated Sleeve

Figure 7:
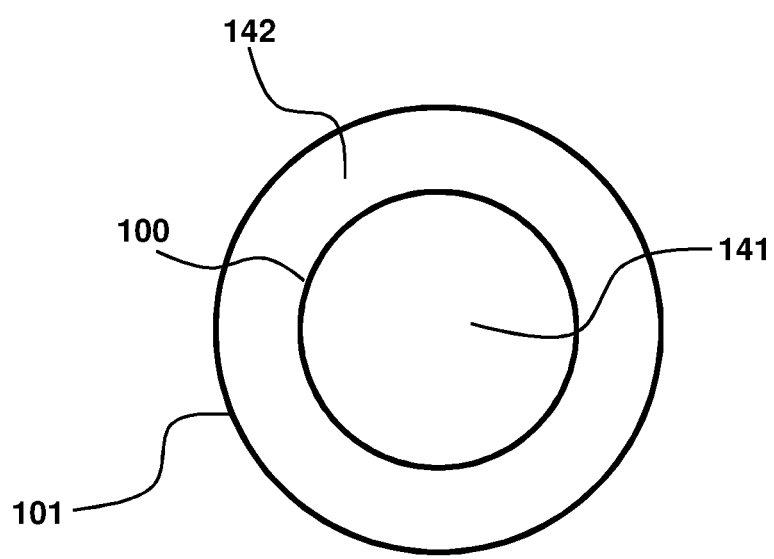
FIG. 7 is a cross-sectional view of the double lumen elongated sleeve.

FIG. 6 and FIG. 7 illustrate a double lumen embodiment, with an inner lumen 141 formed by the elongated sleeve 100 as illustrated in FIG. 1. A second sleeve 101 positioned outside the sleeve 100 forms a second lumen 142 that surrounds the inner lumen 141. A sleeve conduit 421 may provide nutrients to the second lumen for controlled delivery of nutrients. In this aspect, the second sleeve may be formed of a sidewall that is permeable to desired nutrients that are introduced to the patient by sleeve conduit 421. FIG. 7 is a cross-sectional view of a slice of the double lumen, illustrating inner or first lumen 141 and outer or second lumen 142 formed by inner elongated sleeve 100 and outer elongated or second sleeve 101. 100 may be impermeable to the ingested food that has traversed the gastric balloon passage, whereas 101 may be permeable to nutrients and vitamins, including as provided via the third fluid 245 illustrated in FIG. 6.

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups, are disclosed separately. When a Markush group or other grouping is used herein, all individual members of the group and all combinations and subcombinations possible of the group are intended to be individually included in the disclosure.

Every formulation or combination of components described or exemplified herein can be used to practice the invention, unless otherwise stated.

Whenever a range is given in the specification, for example, a size range, an angle range, or a distance range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

We claim:

1. A weight-loss device for treatment of obesity in a patient comprising:
    a gastric balloon configured for positioning in a stomach lumen, said gastric balloon comprising:
    a gastric balloon surface having a gastric balloon surface proximal end and a gastric balloon surface distal end;
    a passage spanning between a passage proximal end at said gastric balloon surface proximal end and a passage distal end at said gastric balloon surface distal end, wherein during use said passage substantially aligns in a direction from an esophageal sphincter toward a pyloric sphincter with said gastric balloon proximal end facing the esophageal sphincter and said gastric balloon distal end facing the pyloric sphincter; and a gastric balloon anchor connected to or extending from said gastric balloon surface configured to reliably position said gastric balloon in a stomach lumen during use;

an elongated sleeve connected to said gastric balloon and configured for insertion into at least a portion of a patient's small intestine during use, said elongated sleeve comprising:

a sleeve wall having an inner-facing surface that forms a sleeve lumen, wherein said sleeve lumen extends from a sleeve proximal end to a sleeve distal end;

wherein said sleeve proximal end is connected to said gastric balloon distal end to provide a continuous pathway extension of said gastric balloon passage; and said sleeve distal end is configured to be positioned during use at a distal region of the small intestine;

wherein said elongated sleeve has a stored configuration adjacent to said gastric balloon surface distal end; wherein said stored configuration is provided by said elongated sleeve that is in a rolled or folded configuration; and said stored configuration corresponds to said elongated sleeve that is within 5 mm of said gastric balloon distal end and a deployed configuration corresponds to a sleeve length between said sleeve distal and proximal ends that is between 50 cm and 500 cm.

2. The device of claim 1, further comprising a transabdominal gastric cannula configured to pass through a stomach wall, wherein said gastric balloon anchor is connected to said transabdominal gastric cannula or a wall of the stomach to position said gastric balloon in the stomach during use.

3. The device of claim 2, further comprising a first port in said transabdominal gastric cannula to accommodate a conduit for introducing and/or removing fluid to vary a volume of said gastric balloon and a diameter of said gastric balloon passage during use.

4. The device of claim 3, further comprising a second port configured to accommodate a funnel conduit to control funnel volume and pressure.

5. The device of claim 4, further comprising a third port configured to accommodate a sleeve conduit configured to introduce vitamins, minerals and nutrients to the small intestine during use of said device.

6. The device of claim 5, wherein said sleeve conduit has:
a proximal end connected to said third port;
a distal end that is in fluid communication with a second lumen of a double lumen elongated sleeve, wherein said second lumen is formed between an inner elongated sleeve and an outer elongated sleeve that circumscribes said inner elongated sleeve, wherein said outer elongated sleeve is permeable and configured to facilitate absorption of vitamins, minerals and nutrients by the small intestine;
wherein said sleeve conduit runs along said gastric balloon surface between said gastric balloon surface distal end to said third port.

7. The device of claim 1, wherein said gastric balloon surface proximal end and passage proximal end are formed into a shape corresponding to a funnel and having a pouch volume, wherein said funnel has a funnel angle of between 15° and 165° and/or a pouch volume of between 30 mL and 300 mL.

8. The device of claim 7, wherein said funnel pouch volume is adjustable and configured to provide patient-individualized control early satiety and fullness.

9. The device of claim 8, further comprising a funnel fluid port operably connected to said gastric balloon surface proximal end for providing a user-controlled pressure to said gastric balloon surface proximal end and to control a funnel shape and volume of said funnel, wherein said funnel shape and volume are adjusted to achieve a desired rate of weight loss in the patient by varying an amount of swallowed food that bypasses said gastric balloon passage; wherein said funnel shape and volume adjustment provides for a controlled percentage of swallowed food that enters said gastric balloon passage that ranges from 15% to 95%.

10. The device of claim 9, further comprising a gastric balloon fluid port connected to an interior volume of said gastric balloon, wherein said gastric balloon fluid port provides a pressurization and volume control of said gastric balloon that is independent of said funnel shape and volume control by said funnel fluid port.

11. The device of claim 1, wherein said elongated sleeve further comprises a double lumen, said double lumen formed by an inner elongated sleeve defining an internal sleeve lumen positioned in an outer circumscribed elongated sleeve, wherein:
said inner elongated sleeve is impermeable to ingested food that is in the internal sleeve lumen; and
said outer elongated sleeve is permeable to minerals, nutrients and vitamins introduced to a second lumen formed between said inner elongated sleeve and said outer elongated sleeve.

12. The device of claim 11, wherein each of said inner elongated sleeve and said outer elongated sleeve proximal ends are connected to said gastric balloon distal end and said double lumen enhances a stiffness of said elongated sleeve to avoid unwanted sleeve twisting during deployment and use.

13. The device of claim 1, further comprising a storage element connected to said gastric balloon surface and in operable connection with said elongated sleeve to store said elongated sleeve adjacent to said gastric balloon surface distal end, wherein said storage element is a removable or severable suture or a removable or severable clip.

14. The device of claim 13, wherein said suture is configured to release said elongated sleeve by an endoscope that traverses said gastric balloon passage or through a transabdominal gastric opening to release or remove said suture and provide said elongated sleeve in said deployed configuration; and wherein said elongated sleeve is configured to operably connect with the endoscope during use to deploy said elongated sleeve in the small intestine by a distally-directed movement of said endoscope relative to said gastric balloon.

15. The device of claim 1, wherein said elongated sleeve connected to said gastric balloon distal end comprises a continuous extension of said gastric balloon distal end.

16. The device of claim 1, wherein said elongated sleeve is formed of a component distinct from said gastric balloon, and said elongated sleeve connected to said gastric balloon is by one or more of: an adhesive, a fastener, a geometric tight fit, or a threaded connector.

17. The device of claim 1, wherein said passage is funnel-shaped to reduce a risk of occlusion, said passage having one or more of:
a maximum diameter toward said passage proximal end that is greater than or equal to 2 cm and less than or equal to 7 cm;
a minimum diameter toward said passage distal end that is greater than or equal to 0.5 cm and less than 2 cm; and/or
a funnel length that is greater than or equal to 1 cm and less than or equal to 50 cm.

18. The device of claim 1, wherein said gastric balloon passage has an adjustable average diameter, with an average passage diameter adjustable from a minimum of 0.5 cm to a maximum of 4 cm.

19. The device of claim 1, further comprising a distal sleeve anchor connected to said sleeve distal end for anchoring said sleeve distal end to the distal region of the small intestine during use, wherein a no-anchor region extends upstream along an entire length of said elongated sleeve from said distal sleeve anchor.

20. The device of claim 1, wherein said sleeve proximal end connected to said distal gastric balloon end provides anchoring of a proximal sleeve portion for reliable positioning of the sleeve proximal end during use without a proximal sleeve anchor.

* * * * *